United States Patent
Sauer et al.

(10) Patent No.: US 8,398,680 B2
(45) Date of Patent: Mar. 19, 2013

(54) BIOABSORBABLE MAGNESIUM KNOTS FOR SECURING SURGICAL SUTURE

(75) Inventors: Jude S. Sauer, Pittsford, NY (US); Heather R. Leigh, Farmington, NY (US)

(73) Assignee: LSI Solutions, Inc., Victor, NY (US)

( * ) Notice: Subject to any disclaimer, the term of this patent is extended or adjusted under 35 U.S.C. 154(b) by 222 days.

(21) Appl. No.: 12/755,943

(22) Filed: Apr. 7, 2010

(65) Prior Publication Data

US 2011/0251641 A1   Oct. 13, 2011

(51) Int. Cl.
*A61B 17/04*   (2006.01)
(52) U.S. Cl. ....................................................... 606/232
(58) Field of Classification Search .................. 606/215, 606/221, 228, 230, 232, 233; 623/13.14
See application file for complete search history.

(56) References Cited

U.S. PATENT DOCUMENTS

| | | |
|---|---|---|
| 3,687,135 A | 8/1972 | Stroganov et al. |
| 3,802,438 A * | 4/1974 | Wolvek .......................... 606/232 |
| 3,875,648 A | 4/1975 | Bone |
| 4,006,474 A | 2/1977 | Lukkarila |
| 4,039,078 A | 8/1977 | Bone |
| 4,235,238 A | 11/1980 | Ogiu et al. |
| 4,448,194 A | 5/1984 | DiGiovanni et al. |
| 4,627,437 A | 12/1986 | Bedi et al. |
| 4,669,473 A | 6/1987 | Richards et al. |
| 4,705,040 A | 11/1987 | Mueller et al. |
| 4,724,840 A | 2/1988 | McVay et al. |
| 4,741,330 A | 5/1988 | Hayhurst |
| 4,841,888 A | 6/1989 | Mills et al. |
| 5,021,059 A | 6/1991 | Kensey et al. |
| 5,041,127 A | 8/1991 | Troutman |
| 5,080,663 A | 1/1992 | Mills et al. |
| 5,085,661 A | 2/1992 | Moss |
| 5,520,702 A | 5/1996 | Sauer et al. |
| 5,643,289 A | 7/1997 | Sauer et al. |
| 5,669,917 A | 9/1997 | Sauer et al. |
| 6,368,334 B1 | 4/2002 | Sauer |
| 6,641,592 B1 | 11/2003 | Sauer et al. |
| 7,235,086 B2 | 6/2007 | Sauer et al. |
| 2002/0120280 A1 * | 8/2002 | Wotton, III ................... 606/148 |
| 2003/0032983 A1 * | 2/2003 | Bonutti et al. ................ 606/232 |
| 2003/0065361 A1 * | 4/2003 | Dreyfuss ....................... 606/232 |
| 2003/0204205 A1 * | 10/2003 | Sauer et al. ................... 606/232 |
| 2006/0020289 A1 | 1/2006 | Kuttler |
| 2007/0055305 A1 | 3/2007 | Schnyder et al. |
| 2007/0270940 A1 * | 11/2007 | Doty ............................ 623/1.22 |
| 2009/0081313 A1 * | 3/2009 | Aghion et al. ................ 424/641 |
| 2009/0248070 A1 | 10/2009 | Kosa et al. |

(Continued)

OTHER PUBLICATIONS http://www.thefreedictionary.com/knot, retrieved Apr. 19, 2012.*

(Continued)

*Primary Examiner* — Ryan Severson
*Assistant Examiner* — David Eastwood
(74) *Attorney, Agent, or Firm* — Stephen B. Salai, Esq.; Harter Secrest & Emery LLP

(57) ABSTRACT

A crimpable magnesium sleeve for securing a suture within the body and for dissolving over time while introducing only compatible amounts of magnesium into the body. An instrument for placing such a sleeve on a suture crimping the sleeve and cutting the suture after placement. An alloy of magnesium, zinc, and aluminum may be used to form the sleeve.

11 Claims, 3 Drawing Sheets

U.S. PATENT DOCUMENTS

2009/0259233 A1 10/2009 Bogart et al.

OTHER PUBLICATIONS http://www.thefreedictionary.com/crimp, retrieved Apr. 19, 2012.*
PCT Notification of Transmittal of the International Search Report and the Written Opinion of the International Searching Authority, or the Declaration (in corresponding PCT Patent Application No. PCT/US2011/021467), dated Sep. 20, 2011 (2 pages).
PCT International Search Report in corresponding PCT Patent Application No. PCT/US2011/021467, dated Sep. 20, 2011 (3 pages).
PCT Written Opinion of the International Searching Authority in corresponding PCT Patent Application No. PCT/US2011/021467, dated Sep. 20, 2011 (4 pages).
Chi T., An Ex-Vivo Evaluation of the Application and Strength of a Novel Laparoscopic Knot Substitute Device, Journal of Endourology 24(1), Jan. 2010: pp. 95-98.
McBride E., Absorbabie Metal in Bone Surgery, JAMA 8 Dec. 31, 1938; 111(27): pp. 2464-2467.
Heublein B., Biocorrosion of Magnesium Alloys: A New Principle Cardiovascular Technology?, Heart Jun. 2003;89 (6): pp. 651-656.
Zartner P., First Successful Implantation of Biodegradable Metal Stent into the Left Pulmonary of a Preterm Baby, Catheter Cardiovascular Interv. Dec. 2005; 66(4). pp. 590-594.
Erne M.. The Road to Bioabsorbable Stents: Reaching Ciinical Reality?, Cardiovascular Intervent Rediol 2006;29: pp. 11-16.
Witte F., In Vivo Corrosion Corrosion of four Magnesium Alloys and the Associated Bone Response, Biomaterials 2005;(26): pp. 3557-3563.
Yibin R., Preliminary Study of Biodegradation of AZ31B Magnesium Alioy, Front Master Sci China 2007;(4): pp. 401-404.
Liu K., Study on Biocompatibility of AZ31B Magnesium Alloy in Mice, China Biotech 2008; 28(3): pp. 63-67.
Cui F., Calcium Phosphate Coating on Magnesium May for Modification of Degradation Behavior, Front Master Sci China 2008; 2(2): pp. 143-148.
YaoHua H., Biocompatibility of Bio-Mg-Zn All Within Bone with Heart, Liver, Kidney and Spleen, Chinese Science Bulletin Feb. 2009; 54(3): pp. 484-491.

* cited by examiner

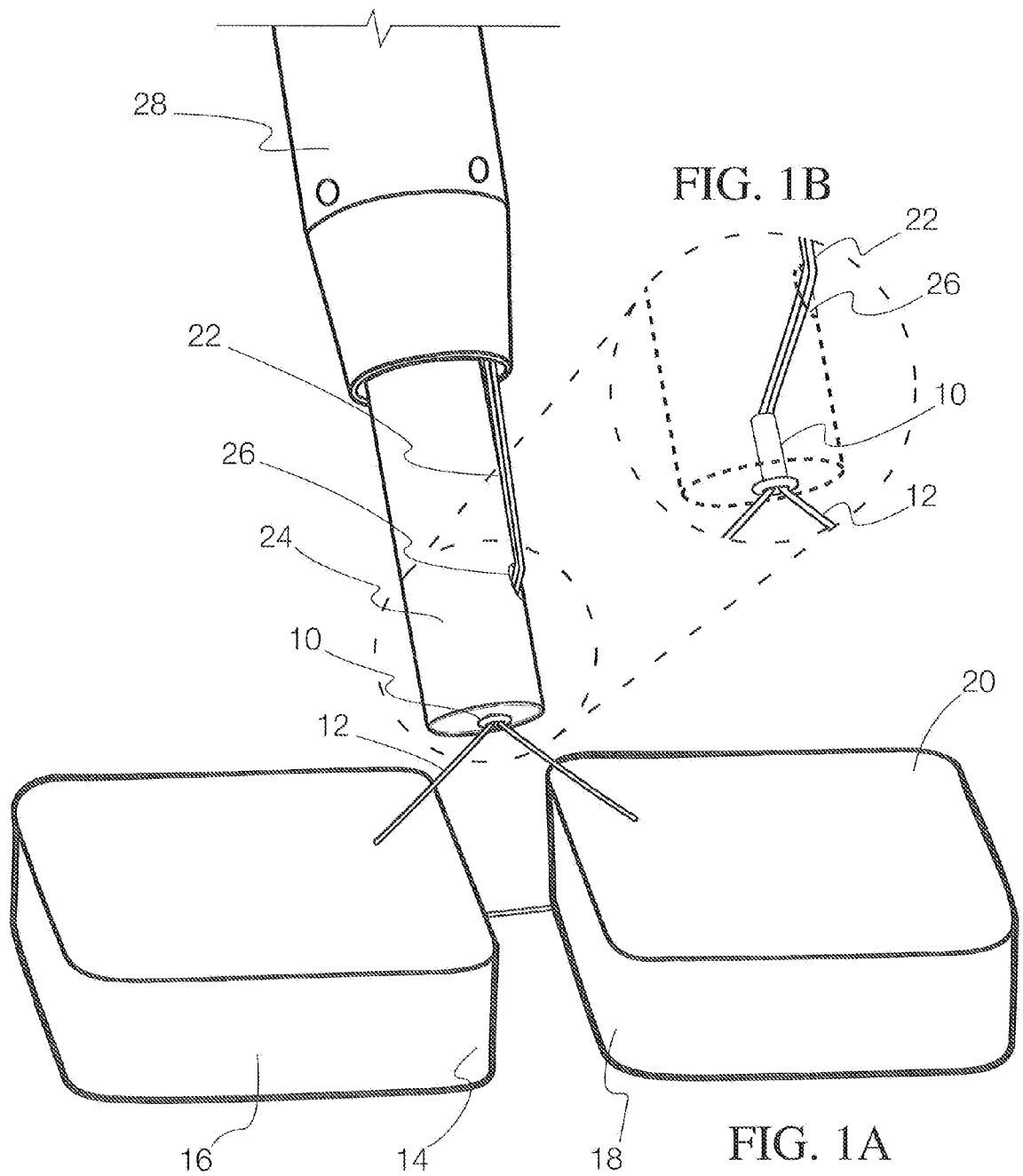

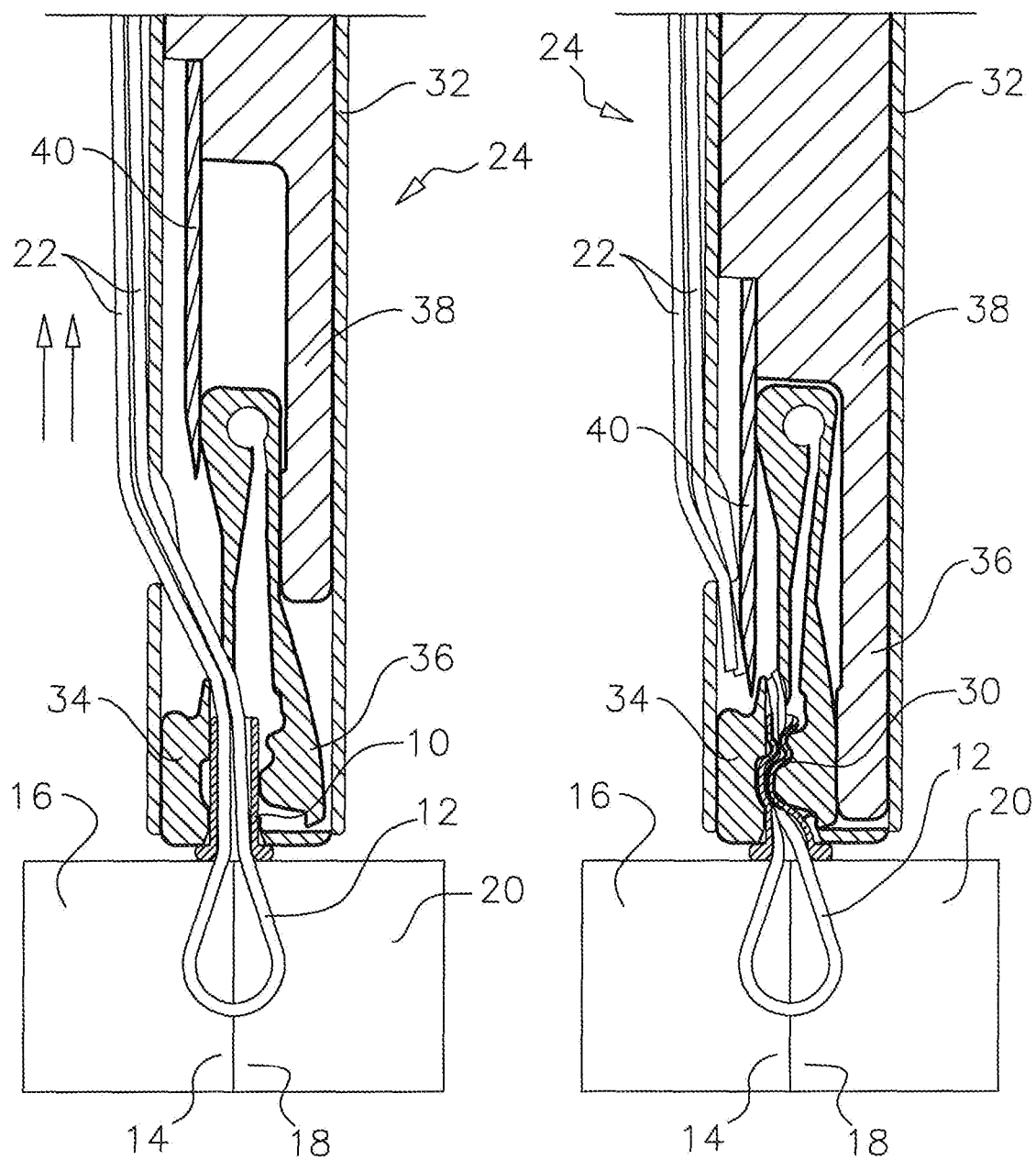
2A  2B

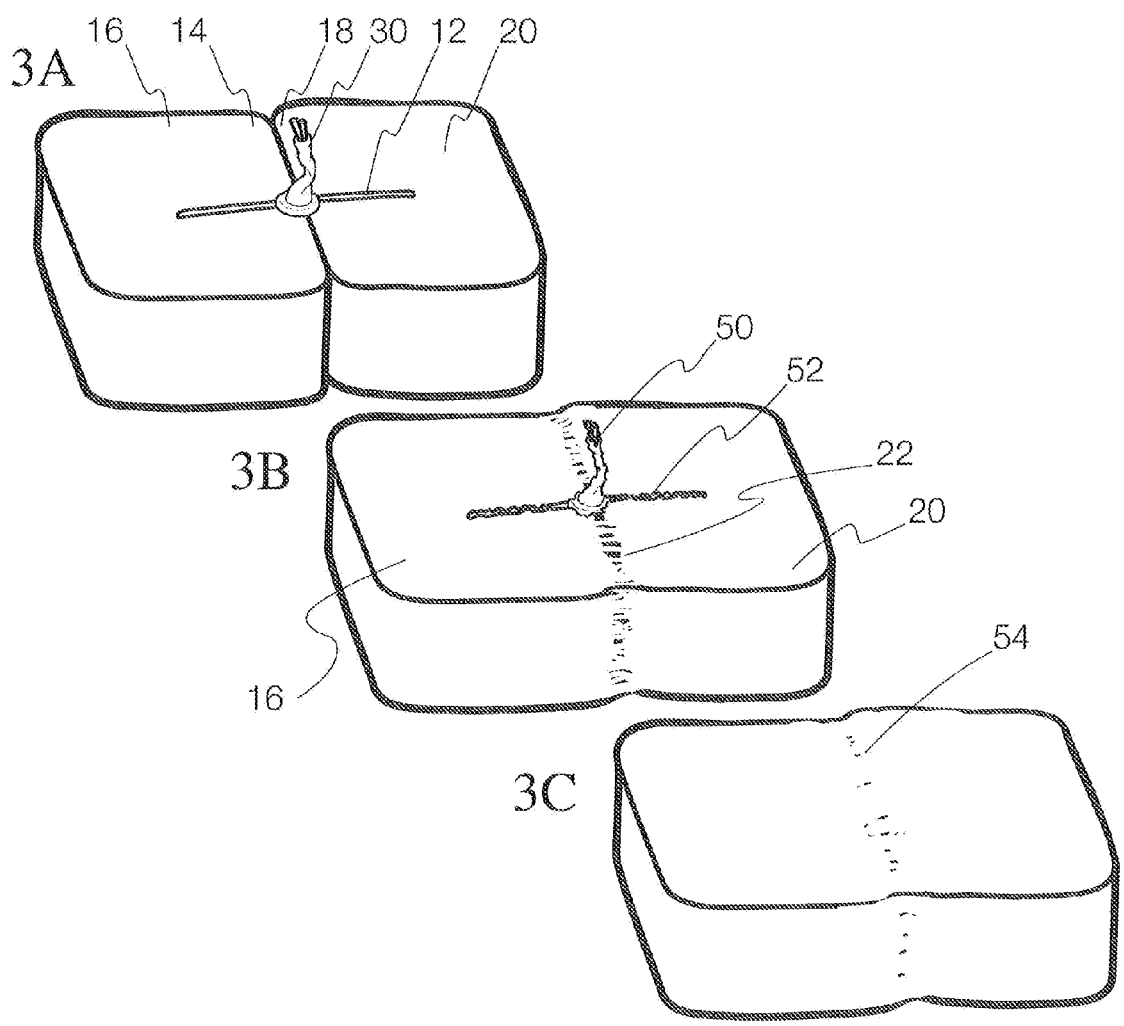

BIOABSORBABLE MAGNESIUM KNOTS FOR SECURING SURGICAL SUTURE

CROSS-REFERENCE TO RELATED APPLICATIONS

None.

STATEMENT REGARDING FEDERALLY SPONSORED RESEARCH OR DEVELOPMENT

None.

NAMES OF THE PARTIES TO A JOINT RESEARCH AGREEMENT

None.

REFERENCE TO A "SEQUENCE LISTING"

None.

BACKGROUND OF THE INVENTION

1. Field of the Invention

This invention relates generally to crimpable metal sleeves used to remotely secure sutures, and more particularly to such sleeves made from magnesium and its alloys.

2. Description of Related Art

A surgeon's ability to hand tie a secure knot in a suture is severely compromised in many minimally invasive surgical procedures. When absorbable sutures are preferred at remote tissue sites, it would be a significant advance to be able to readily create a strong, safe, low profile absorbable knot.

Less invasive therapeutic interventions are most beneficial when the desired physiological or surgical outcome can be achieved with the least amount of iatrogenic trauma to the patient. For example, advances in laparoscopic surgery have proven to be advantageous relative to traditional open surgical procedures, which often require large skin incisions and significant tissue manipulation just to view the surgical site. Both the patient and society benefit from effective minimally invasive surgical procedures by demonstrated reductions in patient pain, hospital stays and recovery time, as well as in the related medical costs.

It is well recognized that advances in minimally invasive surgery require advances in the technology available to physicians to enable effective interventions through size limited access sites. With specialized equipment and imaging methods, hemostatic tissue dissections, specimen removal, wound closure, etc. can often be realized with minimal damage or disruption to surrounding tissues. Over the past several decades, improvements to laparoscopes, video imaging equipment, trocar access ports, surgical insufflation and irrigation systems, graspers, scissors, cautery devices and suturing and stapling devices for wound closer have led to improved patient outcomes.

For most surgeons, however, the remote hand tying of knots in suture through small access ports remains a significant challenge. Laparoscopic hand tying of sutures has been compared to trying to tie one's shoes with chopsticks.

There have been many prior art attempts to circumvent the need for the knotting of suture. Such prior art devices have essentially been staples, clips, clamps or other fasteners (U.S. Pat. Nos. 5,041,127; 5,080,663; 5,021,059; 4,841,888; 4,741,330; 4,724,840; 4,705,040; 4,669,473; 4,627,437; 4,448,194; 4,039,078; 4,235,238; 4,006,747; 3,875,648; 5,085,661).

However, the devices described in the above listed patents do not provide or anticipate the potential advantages of a safe and effective absorbable Magnesium Knot.

Non-absorbable Titanium Knots® delivered through sterile 5 mm Ti-KNOT® TK laparoscopic devices (LSI SOLUTIONS®, Victor, New York, U.S. Pat. Nos. 5,520,702; 5,643,289; 5,669,917; 6,368,334; 6,641,592; 7,235,086) are a currently well accepted commercial alternative to hand tying remote surgical knots. The Titanium Knot® product is based on a surgical crimping technology that deforms a non-absorbable, malleable hollow titanium tube over suture strands to hold them together.

A very recently published study (Chi T. An Ex-Vivo Evaluation of the Application and Strength of a Novel Laparoscopic Knot Substitute Device. J Endourol 24(1):95-98), compared the suture holding strength of traditional hand tied laparoscopic surgical knots (mean tensile strengths 53.0 N, range 27.0-74.9 N) to four different commercially available "laparoscopic knot substitute devices." Note these authors failed to include the very strong, low profile Titanium Knot®, which has been commercially available for over a decade.

The knots tested in this paper included the Suturelock®, ANPA, San Mateo, Calif., mean tensile strength 14.7 N; Lapra-Ty* devices, Ethicon Endosurgery, Piscataway, N.J., 6.1 N; Hem-O-Lock clips, Weck Closure Systems, Research Triangle Park, N.C., 5.4 N; and an unspecified titanium clip, 3.0 N. The authors of this paper note that the hand tied knots "had substantially higher tensile strengths than any of the knot substitutes (P<0.001 for all)" they tested. While the knots tested in the above study were less than half the strength of hand tied suture knots and below USP standards for minimal average knot strength, Titanium Knots® tested under these conditions would have yielded knot strengths comparable to those of hand tied knots.

Healing wounds often require foreign materials, such as non-absorbable polymeric suture or stainless steel staples, clips and knots to provide structural integrity during the initial acute phases of healing. However, in many applications, long-term healing is best enabled without permanent residual foreign bodies. Surgeons frequently elect to use absorbable sutures, such as braided sutures made of polyglycolic acid (PGA) or monofilament sutures made of polydioxanone (PDO), to avoid risks of future discomfort, infection or stone formation instigated by the long-term presence of foreign materials. For remote minimally invasive procedures, when hand tying suture is a difficult option, Titanium Knots® are frequently used in association with both non-absorbable and absorbable suture materials.

The suture loops created by hand tying knots in absorbable suture materials simply biodegrade or re-absorb over time along with the rest of the remaining suture material. When used with an absorbable suture, a Titanium Knot® is left permanently near the wound closure site after the suture material has re-absorbed.

In addition to non-bioabsorbable metals for surgical knots, Sauer (U.S. Pat. No. 5,669,917) proposed a knot-securing member fabricated from a bioabsorbable polymer such as a homopolymer, copolymer or a blend obtained from one or more monomers selected from the group consisting of glycolic acid, lactide, lactic acid p-dioxanne, E-caprolactone and trimethylene carbide. However, multiple attempts of using such bioabsorbable polymers in this application, they have not proved to be an acceptable option. Lapra-Ty* clips can be made of absorbable polymers, but their bulkiness and inherent weakness raises questions regarding their efficacy in critical wound closure applications. To get the suture holding force strength minimally required by United States Pharmacopeia (USP) standards, remotely deployable polymeric-based absorbable knots are simply too big, bulky, and difficult to deploy to be useful in most surgical applications so far.

Magnesium is a remarkable material in a number of relevant ways. While pure magnesium is quite flammable and too rapidly dissolved in the human body, some magnesium alloys have long been recognized for their potential use for non-permanent surgical applications. E. D. McBride first published a paper in 1938. He postulated the exciting opportunity to use this strong metal for internal fixation of fractured bones; the magnesium implant would absorb over time rather than require explantation (McBride E. Absorbable Metal in Bone Surgery. JAMA 8;111(27):2464-2467). Strogenov in 1972 noted some improvements to magnesium using cadmium for surgical orthopedic application (U.S. Pat. No. 3,687,135). Interest in magnesium's implantation for orthopedic applications has waxed and waned throughout the subsequent decades: currently, there are no known commercially available reabsorbable magnesium orthopedic products anywhere in the world.

First reported in 2003, Heublein suggested employing various magnesium based vascular stents to temporarily hold a vessel open during healing (e.g. for opening coronary arteries). (Heublein B. Biocorrosion of Magnesium Alloys: A New Principle in Cardiovascular Implant Technology? Heart 2003;89(6):651-656). Zartner reported in 2005, the first biodegradable stent in the pulmonary artery of an infant (Zartner P. First Successful Implantation of a Biodegradable Metal Stent into the Left Pulmonary of a Preterm Baby. Catheter Cardiovasc Interv. Dec 2005;66(4):590-594.) In 2006, Erne reported, the clinical trials of bioabsorbable vascular stents (Erne M. The Road to Bioabsorbable Stents: Reaching Clinical Reality? Cardiovasc Intervent Radiol 2006;29:11-16.) To our knowledge again, however, no magnesium-based bioabsorbable stents are currently commercially available.

While the use of magnesium alloys for orthopedic structural implants and bio-absorbable stents has been previously reported by others to hold living tissue together (e.g., fractured bones) or apart (e.g., diseased arterial walls), to our knowledge, until now, no one has suggested the surgical use of magnesium alloys to hold non-native foreign materials (i.e., exogenous materials, not intrinsic to the body) like suture. In addition, for previous magnesium alloy medical applications, while all others have proposed using solid rods, wires and screws, our group is the first to describe the use of hollow magnesium components that are crimped together to hold suture materials. In other words, the use of hollow magnesium alloys to temporarily hold together exogenous materials is a new application not obvious to others over the past seven decades; until now, no one has suggested the use of magnesium for absorbable suture knots.

To be clinically relevant, an absorbable knot must be made of a material that has acceptable biocompatibility and excellent strength profiles over specific time periods. Magnesium is found throughout nature and is considered an essential component of the human body. The therapeutic potential of "Epsom salts" rich in magnesium have been recognized since the 17th century. Magnesium is an alkali earth metal from the second main group of the Periodic Table of Elements. This silvery white metal is the eighth most abundant element comprising 2.7% of the earth's crust and 0.13% of sea water. About 30 grams of magnesium is found in a healthy human, mostly in muscle and bone. The U.S. Government has recommended a regular daily adult allowance of magnesium intake of 420 mg/day for males and 320 mg/day for females.

While the degeneration of magnesium by material corrosion, fatigue, erosion, etc., are affected by body variables like temperature, pH, proteins, fluid flows, etc., magnesium alloy mechanical properties can remain substantially strong enough to hold suture together long enough for many healing requirements. Magnesium has the highest strength to weight ratio of all structural metals. Magnesium is 36% lighter per unit volume than aluminum and 78% lighter than iron, both of which are not considered readily biocompatible. Magnesium (~1.8 g/cm$^3$) is substantially less dense than titanium materials (4.5-4.7 g/cm$^3$). Magnesium based materials are available in a wide range of mechanical properties. Magnesium can be machined, cast, formed, welded, heat treated and annealed.

Today's most widely produced magnesium alloy grade is ASTM AZ31 B. A common example is AZ31 B-F magnesium alloy, where the last letter designates the "temper," which here indicates "Fabricated," contains 3% aluminum and 1% zinc by weight and has a tensile strength of 260.0 MPa. Other preferred magnesium alloys incorporate small percentages of rare earth metals and or zirconium and yttrium. Multiple published reports address biocompatibility and relative strength of AZ31 B and other alloys in orthopedic and cardiac applications (Witte F. In Vivo Corrosion of four Magnesium Alloys and the Associated bone Response. Biomaterials 2005;(26):3557-3563. Yibin R. Preliminary Study of Biodegradation of AZ31 B Magnesium Alloy. Front Mater Sci China 2007; (4):401-404. Liu K. Study on Biocompatibility of AZ31 B Magnesium Alloy in Mice. China Biotech 2008;28 (3):63-67. Cui F. Calcium Phosphate Coating on Magnesium Alloy for Modification of Degradation Behavior. Front Mater Sci China 2008;2(2):143-148. YaoHua H. Biocompatibility of Bio-Mg—Zn All Within Bone with Heart, Liver, Kidney and Spleen. Chinese Science Bulletin February 2009;54(3): 484-491.)

BRIEF SUMMARY OF THE INVENTION

A significant clinical need exists for a means for providing a strong, low profile bioabsorbable knot for surgical suture left at some remote wound closure sites. The minimally invasive surgeon cannot simply hand tie knots in absorbable suture at remote sites as is easily achievable in open surgery. While crimped, non-absorbable titanium sleeves have proved highly effective at securing suture together, they remain permanently within the patient. Bioabsorbable polymeric materials have not proved strong or durable enough for reliable, low profile, easy deployment for this application. The present invention is a novel development utilizing biocompatible, malleable, strong and absorbable alloys of magnesium to effectively place an automated remote suture knot that does not remain forever as a permanent foreign material at the suture site.

Our search for a biocompatible malleable and yet strong material for a surgical knot substitute led to the successful evaluation of the metal magnesium in certain alloys. Our research has produced a variety of Magnesium Knots and their delivery devices that have been successfully developed and tested in pre-clinical models. Several Magnesium Knots yielded encouraging results when tested under simulated human body conditions, in human cadavers and in-vivo porcine healing models.

In accordance with one aspect of the invention, a magnesium alloy knot made from AZ31B alloy maintained the ability to hold suture together for a sufficient duration under simulated physiologic conditions. In this embodiment, the Magnesium Knot was shaped like a hollow mushroom and weighed approximately 5.2 grams. This embodiment of a Magnesium Knot has a wall thicknesses about 15% thicker than our current Titanium Knot®.

In accordance with another aspect of the invention, the hammer and anvil structures in the distal tip of the Titanium Knot® crimper are modified to decrease the crimping depth and eliminate corners that concentrate stresses so that crimping between the hammer and anvil did not cause cracking of the Magnesium Knot.

In accordance with another aspect of this invention, the finished Magnesium Knots are rapidly heated in an argon gas environment to 650° F. and maintained at that temperature for two hours. The Knots are then cooled gradually to room temperature over approximately four hours.

Magnesium Knots made from other combinations of alloys and with thinner walls or not including the custom heat treats tended to crack during the crimping process. Such cracks rapidly degraded the structural integrity of a Magnesium Knot under physiologic conditions, leading to rapid loss of suture holding strength. This rapid loss yielded knots that would fail before tissue would have time to heal.

These preferred embodiments have acceptable characteristics and positive results in table top testing and in human cadaver models and have lead to further testing in in-vivo porcine models. Using laparoscopic techniques, 41 Magnesium Knots were placed at varying tissue sites securing a variety of suture types in the abdominal cavities of three pigs. These knots were subsequently harvested at one, two and three week intervals post-op. Successful healing was demonstrated at gastric, urinary bladder and uterine tissue sites. Magnesium Knots, placed both from the inside and the outside of the urinary bladder, were also effective over this critical three week time interval in closing wounds in the bladder wall.

BRIEF DESCRIPTION OF THE SEVERAL VIEWS OF THE DRAWING

FIG. 1A is a perspective view of a Magnesium Knot within its delivery device over suture approaching a wound closure site.

FIG. 1B is a close-up perspective view of a Magnesium Knot and suture now shown with its delivery device hidden.

FIG. 2A is a cross-sectional view showing an un-crimped Magnesium Knot in the distal end of its delivery device positioned over suture upon apposed tissue edges.

FIG. 2B is a cross-sectional view of a crimped Magnesium Knot within the distal end of its delivery device still positioned upon opposed tissue edges, but now with suture tails cut.

FIG. 3A shows a crimped Magnesium Knot immediately after release from its delivery device securing suture together to hold tissue wound edges in apposition.

FIG. 3B shows a Magnesium Knot and its suture partially absorbed during an early phase of wound healing.

FIG. 3C shows the wound healing site at a later phase of wound healing after the Magnesium Knot and suture are no longer present.

DETAILED DESCRIPTION OF THE INVENTION

Referring to FIG. 1A, the Magnesium Knot 10 in accordance with an aspect of the present invention is shown in perspective view held within the distal tip of it delivery device 24, which also provides a suture exit hole 26. The relationship between a suture loop 12 and the Magnesium Knot 10 is illustrated to show the suture loop coursing and looping through both an apposing edge 14 of the left side of tissue wound segment 16 and a corresponding apposing edge 18 of the right side of tissue wound segment 20. Note that by advancing the Magnesium Knot 10 toward tissue segments 16 and 20 and by pulling the suture tails 22, the wound edges 14 and 18 can be drawn together into intimate apposition to optimize healing. Also note that a tubular cannula 28 is shown to illustrate a device through which the Magnesium Knot delivery device 24 and suture tails 22 can pass into the patient.

FIG. 1B shows a close-up of the Magnesium Knot 10 and suture 12, 22 of FIG. 1A now with the tip of its delivery device 24 hidden to reveal the course of the suture as it passes through the Magnesium Knot 10 through the inside of its delivery device and out through the suture hole 26.

For example, one preferred magnesium alloy knot embodiment, made from AZ31B alloy, maintained the ability to hold suture together for a sufficient duration under simulated physiologic conditions. In this embodiment, the Magnesium Knot was shaped like a hollow mushroom and weighed approximately 5.2 grams. While generally similar in shape to our current commercialized Titanium Knot®, this embodiment of a Magnesium Knot required wall thicknesses about 15% thicker than our current Titanium Knot®. This embodiment also required the shapes of the hammer and anvil structures in the distal tip of the Titanium Knot® crimper to be rounded and the depth of crimping reduced so that crimping between the hammer anvil did not cause cracking of the Magnesium Knot. It further required the development of a customized heat treating process to avoid cracking during crimping. For example, in accordance with an exemplary heat treating process, the finished Magnesium Knots are rapidly heated in an argon gas environment to at least 600° F., preferably 650° F. and maintained at that temperature for at least one hour, preferably two hours. The Knots are then cooled gradually to room temperature over approximately two hours, more preferably four hours.

When applied to 2-0 absorbable suture bathed at body temperature in a physiologic solution model, this Magnesium Knot's holding strength exceeded the holding strength requirement of 1.44 kg tensile strength on the USP non-absorbable suture for up to two weeks (i.e., 6.8, 5.4, 3.8, 3.6, 3.5 and 2.3 kg f at 0, 3, 6, 9, 12 and 15 days, respectively). Note, each of these magnesium alloy knots would represent approximately 1% and 0.3% of the United States Department of Agriculture (USDA) recommended daily allowance for magnesium and zinc, plus about 2% of the estimated average daily adult oral intake of aluminum.

In accordance with a presently preferred embodiment of this invention for use 2-0 size suture, the overall length of the Magnesium Knot 10 is preferably about 0.130±0.002 inches and the diameter of the mushroom cap or crown is 0.080±0.005 inches. The inside diameter of the elongated tubular portion is preferably about 0.035±0.005 inches and the outside diameter is approximately 0.0520±0.001 inches so that the wall thickness ranges from about 0.0078 to 0.0093 inches. For other suture sizes, the wall thickness will range from 0.002 to 0.019 inches. This is approximately 20% thicker than known knots and provides the characteristics described herein. While these dimensions have produced Knots that hold securely and do not crack, the dimensions may be changed as long as the secure holding and resistance to cracking are maintained.

FIG. 2A and FIG. 2B show in cross-section the pre-crimped Magnesium Knot 10 and the crimped Magnesium Knot 30, respectively, held into the distal end of their delivery devices 24. The distal end of the delivery device consists of a tubular shaft tube 32 which is fixed to a structure providing an immobilized anvil 34 and deployable hammer 36.

FIG. 2A shows mobile hammer 36 holding the un-crimped Magnesium Knot 10 between itself and fixed anvil 34. Wedge tip 38 with its attached suture blade 40 are in their most proximal position with the Magnesium Knot 10 adjacent to the wound closure site and with tension applied to the suture tails 22 (double arrows), so that the apposing wound edges 14 and 18 of tissue segments 16 and 20 are held together.

FIG. 2B shows the now crimped Magnesium Knot 30 compressed between the fixed anvil 34 and the mobile hammer 36, which was driven down towards the fixed anvil 34 by the distal advancement of wedge tip 38, thereby compressing Magnesium Knot 30. The suture blade 40 which advances distally is attached to wedge tip 38 and transects the suture tails 22 above the crimped Magnesium Knot 30. Upon retraction of wedge tip 38 and its suture blade 40, the crimped Magnesium Knot 30 and its secured suture loop 12 are released from the delivery device, which is removed from the surgical site. The suture loop 12 is secured by the crimped Magnesium Knot 30 to hold together edges 14 and 18 from tissue segments 16 and 20.

FIG. 3A, FIG. 3B and FIG. 3C highlight the results of deploying a Magnesium Knot at a wound closure site upon acute deployment, at an intermediate healing stage when the Magnesium Knot and the absorbable suture still provide structural integrity and at a later stage when the healing wound no longer benefits from the presence of the Magnesium Knot or suture, respectively.

FIG. 3A shows the crimped Magnesium Knot 30 and the free ends of suture loop 12 soon after deployment. Wound edges 14 and 18 are held together by the Magnesium Knot 30 and suture loop 12 to provide apposition for tissue segments 16 and 20.

FIG. 3B shows the same wound site of FIG. 3A, but now after the passage of time. The previously separate wound edges have begun to heal together re-establishing the intimate tissue plane 22 between tissue segments 16 and 20. The partially absorbed Magnesium Knot 50 shows an erosive loss of material along with material loss evident on the absorbing suture 52.

FIG. 3C shows the same wound closure site as shown in FIG. 3A and FIG. 3B now with all of the foreign magnesium alloy and suture material gone from the site of installation. At this stage, the tissue has remodeled so the previously separated wound edges become an almost indistinguishable healed zone 54.

While the invention has been described in connection with several presently preferred embodiments thereof, those skilled in the art will recognize that certain modifications and changes may be made therein without departing from the true spirit and scope of the invention which accordingly is intended to be defined solely by the appended claims.

The invention claimed is:

1. An absorbable knot for a suture consisting essentially of magnesium and one or more biocompatible alloying metals each present in an amount that is non-toxic at the rate at which the metal is released into the body as the knot is absorbed in which the one or more alloying biocompatible metals are selected from the group consisting of iron, aluminum, and zinc, in which the one or more biocompatible alloying metals are present in amounts such that the resulting alloy can be crimped on a suture without cracking, and in which the absorbable knot comprises a wall having a thickness between about 0.002 inches and 0.019 inches, said wall thickness selected so that the absorbable knot can be crimped on a suture without cracking, the absorbable knot comprising about 1% by weight of zinc and about 3% by weight of aluminum.

2. An absorbable knot for a suture comprising magnesium and one or more alloying metals each present in an amount that is non-toxic at the rate at which the metal is released into the body as the knot is absorbed, wherein the one or more alloying metals are selected from the group consisting of iron, aluminum, and zinc, and in which the absorbable knot comprises a wall having a thickness between about 0.002 inches and 0.019 inches, said wall thickness selected so that the absorbable knot can be crimped on a suture without cracking.

3. The absorbable knot of claim 2 in which the one or more biocompatible alloying metals are present in amounts such that the resulting alloy can be crimped on a suture without cracking.

4. The absorbable knot of claim 3 comprising about 1% by weight of zinc and about 3% by weight of aluminum.

5. The absorbable knot of claim 1, further wherein the wall thickness of the absorbable knot is between 0.0078 and 0.0093 inches.

6. The absorbable knot of claim 1 wherein the knot comprises AZ31B alloy.

7. The absorbable knot of claim 2, further wherein the wall thickness of the absorbable knot is between 0.0078 and 0.0093 inches.

8. The absorbable knot of claim 2 wherein the knot comprises AZ31B alloy.

9. The absorbable knot of claim 1 wherein the knot comprises a tubular member and wherein the suture passes through the tubular member prior to crimping.

10. The absorbable knot of claim 2 wherein the knot comprises a tubular member and wherein the suture passes through the tubular member prior to crimping.

11. The absorbable knot of claim 2 wherein aluminum and zinc are selected as the alloying biocompatible metals.

* * * * *